US006306795B1

(12) United States Patent
Ryan et al.

(10) Patent No.: US 6,306,795 B1
(45) Date of Patent: Oct. 23, 2001

(54) STABLE HIGHLY ACTIVE SUPPORTED COPPER BASED CATALYSTS

(75) Inventors: Mark Donal Ryan, Stamford, CT (US); John Bradley Roucis, River Ridge, LA (US); James Donald Carruthers, Fairfield, CT (US)

(73) Assignee: Cytec Technology Corp., Wilmington, DE (US)

(*) Notice: Subject to any disclaimer, the term of this patent is extended or adjusted under 35 U.S.C. 154(b) by 0 days.

(21) Appl. No.: 09/390,917

(22) Filed: Sep. 7, 1999

(51) Int. Cl.[7] ............................. B01J 23/70; B01J 23/72; B01J 23/00; B01J 23/08; C01F 7/02
(52) U.S. Cl. ........................ 502/346; 502/355; 423/628; 423/604
(58) Field of Search .................... 502/346, 355; 423/628, 604

(56) References Cited

U.S. PATENT DOCUMENTS

| | | | |
|---|---|---|---|
| 3,631,104 | 12/1971 | Habermann et al. | 260/561 N |
| 3,654,161 | 4/1972 | Geus | 252/62.56 |
| 3,699,164 | 10/1972 | Fine et al. | 260/561 N |
| 3,758,578 | 9/1973 | Habermann et al. | 260/561 N |
| 3,766,088 | 10/1973 | Yoshimura et al. | 252/412 |
| 3,767,706 | 10/1973 | Habermann et al. | 260/561 N |
| 3,787,332 | 1/1974 | Sugier | 106/65 |
| 3,869,511 | 3/1975 | Johnson et al. | 260/561 N |
| 3,900,517 | * 8/1975 | Svarz | 260/561 N |
| 3,925,481 | 12/1975 | Geus | 260/597 R |
| 3,936,502 | 2/1976 | Barber | 260/561 N |
| 3,944,609 | 3/1976 | Fetchin et al. | 260/561 N |
| 3,985,806 | 10/1976 | Hashimoto et al. | 260/561 N |
| 3,994,973 | 11/1976 | Habermann et al. | 260/561 N |
| 4,009,124 | 2/1977 | Laurer et al. | 252/463 |
| 4,028,223 | 6/1977 | Hayes et al. | 208/91 |
| 4,040,980 | * 8/1977 | Matsuda et al. | 252/463 |
| 4,042,532 | 8/1977 | McArthur | 252/466 J |
| 4,062,899 | 12/1977 | Laurer et al. | 260/635 Y |
| 4,113,658 | 9/1978 | Geus | 252/454 |
| 4,191,664 | 3/1980 | McArthur | 252/466 J |
| 4,206,148 | 6/1980 | Biola et al. | 260/578 |
| 4,209,424 | 6/1980 | LeGoff et al. | 252/474 |
| 4,224,191 | 9/1980 | Bishop, III | 252/463 |
| 4,234,727 | 11/1980 | Toussaint et al. | 544/178 |
| 4,259,213 | 3/1981 | Bishop, III | 252/463 |
| 4,302,597 | 11/1981 | Manara et al. | 564/127 |
| 4,308,176 | 12/1981 | Kristiansen | 252/463 |
| 4,329,500 | 5/1982 | Habermann | 564/128 |
| 4,345,101 | 8/1982 | Asano et al. | 564/206 |
| 4,365,090 | 12/1982 | Asano | 564/127 |
| 4,365,091 | 12/1982 | Masaaki et al. | 564/127 |
| 4,388,225 | 6/1983 | Solomon | 252/463 |
| 4,440,956 | 4/1984 | Couvillion | 585/260 |
| 4,490,480 | 12/1984 | Lok et al. | 502/315 |
| 4,493,906 | 1/1985 | Couvillion | 502/346 |
| 4,504,596 | * 3/1985 | Schoepe et al. | 502/225 |
| 4,504,597 | 3/1985 | Klar et al. | 502/225 |
| 4,543,423 | 9/1985 | Farrar et al. | 564/128 |
| 4,629,612 | 12/1986 | van der Wal et al. | 423/244 |
| 4,631,266 | 12/1986 | Wold et al. | 502/324 |
| 4,711,773 | 12/1987 | Mesters et al. | 423/655 |
| 4,867,882 | 9/1989 | O'Neill et al. | 210/684 |
| 4,916,108 | 4/1990 | Mclaughlin et al. | 502/337 |
| 4,946,821 | * 8/1990 | Oudejans et al. | 502/335 |
| 5,012,025 | 4/1991 | Sankaran | 585/415 |
| 5,041,656 | 8/1991 | Asano et al. | 564/127 |
| 5,126,310 | * 6/1992 | Golden et al. | 502/417 |
| 5,242,883 | 9/1993 | Ichikawa et al. | 502/439 |
| 5,298,472 | * 3/1994 | Wegman et al. | 502/346 |
| 5,345,005 | 9/1994 | Thakur et al. | 568/885 |
| 5,476,883 | 12/1995 | Abe et al. | 523/310 |
| 5,534,655 | 7/1996 | Kambara et al. | 564/127 |
| 5,540,981 | 7/1996 | Gallagher et al. | 428/220 |
| 5,541,147 | 7/1996 | Friedlander et al. | 502/100 |
| 5,591,873 | 1/1997 | Bankmann et al. | 549/503 |
| 5,759,939 | 6/1998 | Klabunde et al. | 502/328 |
| 5,817,872 | 10/1998 | Honda et al. | 564/127 |
| 6,015,485 | * 1/2000 | Shukis et al. | 208/112 |

FOREIGN PATENT DOCUMENTS

| | | |
|---|---|---|
| 0 434 061 | 6/1991 | (EP). |
| 0 635 484 | 1/1995 | (EP). |
| 0 695 579 | 2/1996 | (EP). |
| 1324509 | 7/1973 | (GB). |
| 166044 | 8/1987 | (IN). |
| WO 95/31280 | 11/1995 | (WO). |

OTHER PUBLICATIONS

Hayashi et al., 1981, "Selective Conversion of Nitriles to Amides over Suspended Copper Catalysts", J. Catalysis 69:44–50 (Dec. 1980).

Kaushik and Ravindranathan, 1992, "X.P.S. Study of Copper–Containing Y Zeolites for the Hydration of Acrylonitrile to Acrylamide", Zeolites 12:415–419 (Nov. 1991).

Miura et al., 1982, "Selective Hydration of Acrylonitrile on Metal Oxide Catalysts", Chem. Lett., pp. 183–186 month not avail.

Nozaki et al., 1983, "Selective Hydration of Acrylonitrile to Acrylamide over a Manganese Dioxide Catalyst", J. Catalysis 84:267–269 month not avail.

(List continued on next page.)

*Primary Examiner*—Mark L. Bell
*Assistant Examiner*—Patricia L. Hailey
(74) *Attorney, Agent, or Firm*—Pennie & Edmonds LLP

(57) ABSTRACT

Stable highly active supported copper based catalysts are comprised of copper oxide or elemental copper crystallites supported on mechanically stable aluminum oxide and are characterized by high surface area, small copper crystallite size, and high metal loading. The average crystallite size of the copper compound is from about 20 to about 300 Å, the copper loading is from about 10 to about 35 weight percent, the average particle diameter is from about 0.1 mm to about 10 mm, and the total surface area is from about 20 to about 400 square meters per gram. The catalysts are useful for hydration of nitriles to amides, especially hydration of acrylonitrile to acrylamide. The catalysts are distinguished by high mechanical stability, extended lifetime, and excellent resistance to hydration and copper leaching.

43 Claims, No Drawings

OTHER PUBLICATIONS

Otsuka et al., 1975, "Development of Catalytic Hydration Process for Acrylamide Production", Chem Economy & Engineering Rev. 7:29–32 Apr. 1975.

Parkins, 1996, "Catalytic Hydration of Nitriles to Amides", Platinum Metals Rev. 40:169–174 month N/A.

Toshima and Wang, 1994, "Preparation and Catalysis of Novel Colloidal Dispersions of Copper/Noble Metal Bimetallic Clusters", Langmuir 10:4574–4580 Sep. 1994.

* cited by examiner

STABLE HIGHLY ACTIVE SUPPORTED COPPER BASED CATALYSTS

TECHNICAL FIELD

This invention relates to highly active supported copper based catalysts. More particularly, this invention is directed to mechanically stable aluminum oxide supported copper based catalysts useful, e.g., for hydration of nitriles to amides, especially for the hydration of acrylonitrile to acrylamide.

BACKGROUND OF THE INVENTION

Acrylamide is considered the most commercially important of the acrylic and methacrylic amides. It is useful, for example, for waste water treatment, soil stabilization, papermaking, manufacture of polymers, and as an additive for textiles, paints, and cement. Industrially, acrylamide is manufactured by acrylonitrile hydration.

Early commercial nitrile hydration was mediated by sulfuric acid. But this environmentally unfriendly process required expensive equipment and presented waste disposal problems. Subsequently, the acid mediated process was abandoned in favor of metal catalyzed hydration. Beginning in 1971, a series of patents issued that described various unsupported elemental copper based nitrile hydration catalysts, some of which have since achieved commercial success; i.e., U.S. Pat. Nos. 3,597,481; 3,631,104; 3,342,894; 3,642,643; 3,642,913; 3,696,152; 3,758,578; and 3,767,706. Since then, hundreds of variations and improvements have been disclosed and the topic has been reviewed (E. Otsuka et al. *Chem. Econ. Eng. Rev.* 7(4), 29, (1979)).

Of the unsupported elemental copper catalysts, Raney copper is one of the most popular for commercial scale acrylonitrile hydration (See, e.g., U.S. Pat. No. 3,767,706 and U.S. Pat. No. 3,985,806) because of its high surface area and activity per unit copper metal relative to other forms of elemental copper. Preparation comprises leaching an alloy of copper and aluminum with a strong base. But an inherent problem with elemental copper is inefficient metal utilization and therefore high loading is required to achieve reasonable reaction rates and conversions. Another significant drawback of elemental copper hydration catalysts is the limited lifetime, that is, over a period of days to weeks of continuous use, a gradual decrease in activity is observed. Yet another disadvantage is low mechanical stability and catalyst fragmentation into increasingly fine particles. This causes variations in catalyst surface area so that, even if other conditions are maintained, the amount of reaction per catalyst unit will vary and, as a consequence, the conversion rate will be erratic and the catalyst lifetime will be reduced.

Some problems with these elemental metal catalysts can be mitigated, in certain applications, by depositing the metal onto a substrate support. As is well known in the art, supported metals generally have higher surface areas—and thus higher activities—per unit metal than their unsupported counterparts. Hence, with supported catalysts, the metal is used much more efficiently and this, of course, is economically advantageous. One reason for the higher surface area is that the metal can be dispersed on the solid substrate support as small crystallites. This favorable trend, however, is undermined because it is difficult to impregnate supports with small metal crystallites (i.e., having a high metal surface area per unit metal) while simultaneously achieving high metal loading.

The art relating to metals and promoters supported on aluminum oxide ($Al_2O_3$ or alumina) is mature and the references are numerous. Activated aluminum oxide is available via dehydration of the hydrated form ($Al_2O_{(3-x)}(OH)_{2x}$). Several types of hydrated aluminum oxide are readily available, including Gibbsite and Bayerite (Al$(OH)_3$). Loss of a molecule of water leads to the oxyhydroxides (AlO(OH)), boehmite, pseudo boehmite, and diaspore (for reviews see: Augustine R. L. , Heterogeneous catalysis for the Synthetic Chemist, Marcel Dekker, Inc. New York, N.Y. (1996) pp. 161–163 and *The Encyclopedia of Chemical Technology*, 2 Kirk-Othomer ($4^{th}$ ed. at 426)) both of which are incorporated herein by reference.

Significantly, it is known that aluminum oxide's surface area, mechanical stability, and resistance to hydration are highly dependent upon the temperature at which the aluminum oxide is calcined. In general, as hydrous aluminum oxide is calcined, water is driven off, leaving a porous solid structure of activated aluminum oxide. Simple drying of aluminum oxide at temperatures lower than about 500° C. affords aluminum oxide that has relatively low mechanical stability and low water reabsorption resistance. On the other hand, calcination between about 550° C. to 850° C. affords the more mechanically stable and hydration resistant gamma aluminum oxide phase (γ-alumina), which has a surface area of about 150 to 300 $m^2$/g. Further heating (875 to 1150° C.) effects further phase shift through delta-alumina (δ-alumina), to theta-alumina (θ-alumina), and finally to the alpha-alumina (α-alumina) phase. This phase change—i.e., γ-,δ-,θ-, to α-alumina—is accompanied by increased mechanical stability and increased hydration resistance. Resistance to rehydration is very important to a catalyst's stability and lifetime under aqueous phase reaction conditions (e.g., in hydration reactions). High resistance to rehydration correlates with improved structural integrity. But on the downside, the phase change through γ-, δ-, θ- to α-alumina is accompanied by surface area reduction (i.e., to about 5 $m^2$/g for α-alumina). Accordingly, for the purposes of the present invention, the phrase: mechanically stable aluminum oxide phase; refers to either γ-,δ-,θ-, or α-alumina or any mixture thereof.

In short, γ-,δ-,θ-, and α-alumina are favorable supports in view of their good hydration resistance and high mechanical stability. But a disadvantage of γ-,δ-,θ-, and α-alumina as catalyst supports is that the derived metal catalysts are expected to have relatively low activity per unit copper metal.

Disclosures of catalyst compositions comprised of elemental copper and copper oxide supported on aluminum oxide and preparation methods are widespread. In general, a copper salt is bonded to the aluminum oxide support and the support-copper salt complex is calcined to convert the copper salt to copper oxide. If desired, the copper oxide crystallites may be converted to elemental copper by chemical reduction.

One popular procedure for preparation of aluminum oxide supported copper oxide based catalysts is the single pore volume impregnation procedure (or PVI, also known as the incipient wetness procedure). One variation of the pore volume impregnation procedure comprises saturating the pores of an aluminum oxide phase with aqueous copper salt solution, drying, then calcining the impregnated aluminum oxide to convert the copper salt to copper oxide. Unfortunately, this single impregnation procedure affords relatively large metal crystallites concentrated at the surface of the support particle. For an example see M. Kotter et al. Delmon et al. editors *Preparation of Catalysis II*, Elsevier Scientific Publishing Company, New York (1979) p. 51–62.

As disclosed in the three references discussed below, a second version of the pore volume impregnation procedure involves a double impregnation technique. This procedure is similar to the single PVI procedure above, but in the first impregnation, a metal chelating agent is bound to the catalyst support. In the second impregnation, the pre-doped support is contacted with an aqueous metal salt solution, dried, and calcined as above. But this process, in general, does not yield catalysts characterized by high metal loading simultaneously with small metal crystallite size. Accordingly, high activities per unit metal are not achieved.

In the first reference, Barcicki et al. (*React. Kinet. Catal. Lett.*, Vol 17, No. 1–2, 169–173 (1981))—incorporated herein by reference—discloses nickel catalysts characterized by small metal crystallites in the range of 20 to 30 Å supported on γ-alumina. But in the best case, the nickel loading was only about 3 weight percent.

In a second reference, Nazimek (*Applied Catalysis* 12 (1984) 227–236) presents a study of the alkane hydrogenolysis reaction rate dependence on nickel crystallite size. The nickel's average crystallite size ranges from about 15 Å to about 120 Å, however, similar to the catalyst described above, the metal loading was only about 0.5 to about 2 weight percent.

In a third reference, WO 95/31280, another double impregnation procedure was disclosed.

The above single or double pore volume impregnation procedures allow manipulation of the aluminum oxide phase (e.g., calcination to achieve mechanically stable aluminum oxide) prior to metal introduction. But, if such a procedure is used to impregnate γ-, δ-, θ-, and α-alumina, then high surface area, high metal loading, and small metal crystallite size are difficult to achieve. One explanation for this is that the more mechanically stable aluminum oxide phase supports have relatively low surface areas, and the art, in general, teaches that the lower the surface area of the aluminum oxide support, the more difficult it is to achieve small metal crystallite size, simultaneously with high loading of a subsequently impregnated metal.

Co-precipitation is another procedure for the preparation of aluminum oxide supported copper oxide crystallites. This procedure yields aluminum oxide supported catalysts with high surface area, high metal loading, and small metal crystallite size. Disadvantages are that co-precipitated type copper-aluminum oxide catalysts have low mechanical stability (i.e., the aluminum oxide support exists in the unstable amorphous phase rather than in the mechanically stable γ-, δ-, θ-, or α-phases) and relatively low activity per unit copper metal. Even further, co-precipitated copper on aluminum oxide catalysts tend to leach copper during aqueous phase reactions. A high copper content in the effluent indicates a greater degree of leaching that, of course, shortens the catalyst's life and can have a negative impact on the quality of the final acrylamide product solution in commercial applications.

The co-precipitation procedure for making copper on aluminum oxide should be distinguished from the impregnation methods discussed above. With co-precipitation, the aluminum oxide-copper salt complex is formed directly in solution. Thus, pretreatment of the aluminum oxide phase (e.g., calcination to achieve mechanically stable γ-, δ-, θ-, or α-aluminum oxide phases), before the metal is introduced, is impossible. So, in the co-precipitation case, while high surface area, high metal loading, and small metal crystallite size are obtainable, the aluminum oxide is formed in the unstable amorphous phase rather than in the mechanically stable γ-, δ-, θ-, or α-phases. Any attempt to improve the stability of the co-precipitated type catalyst, by calcination at temperatures over about 650° C., generally results in copper crystallite sintering. Concerning co-precipitated catalyst's low relative activity per unit copper metal, this may be due to partial occlusion of the copper source within the aluminum oxide matrix. Hence, the copper metal is not available for reaction. A more efficient arrangement is to have the active material distributed on the surface area throughout the particle. (Augustine R. L., Heterogeneous catalysis for the Synthetic Chemist, p. 271, Marcel Dekker, Inc. (1996)).

For an example see German laid open application DOS 2,445,303 (corresponding to U.S. Pat. Nos. 4,009,124 and 4,062,899), which discloses base treatment of an aqueous copper salt (e.g., copper nitrate) and aluminum salt (e.g., aluminum nitrate) solution to precipitate a mixture of copper and aluminum oxides. This precipitated powder is filtered and calcined at 350 to 600° C. Additional patents describing co-precipitated catalysts include U.S. Pat. Nos. 5,817,872 4,631,266, and 4,386,018 and European Patent Application 0434,061 B1.

Another procedure, which can be utilized for the preparation of copper oxide crystallites on an aluminum oxide support, is called precipitation-deposition. The process comprises inducing precipitation of a dissolved metal species which then deposits upon a finely powdered solid support. Precipitation of the dissolved metal species can be induced by changing the solution pH, decomplexation to an insoluble metal ion, or oxidation or reduction techniques, etc.

The precipitation-deposition procedure is exemplified in U.S. Pat. No. 4,113,658 to Geus. Geus discloses a precipitation-deposition procedure to prepare supported metal catalysts characterized by small metal crystallite size (about 50 to 300 Å) and high metal loading (e.g., 50% by weight or more). The final catalyst (i.e., metal species/support composite) is in the form of a fine powder of particle size between about 100 to about 3000 Å. After the precipitation/deposition, the catalyst may be treated by subsequent heating, oxidation, or reduction to form other catalytically active species.

A primary disadvantage of precipitation/deposition is that finely powdered catalysts result. Catalysts in the form of fine powders are not suitable for fixed bed reactor use. Generally, for use in a fixed bed reactor, a catalyst pellet size of about 1.5 mm to about 10 mm in diameter is required. What is more, the fine powdered catalysts prepared by precipitation/deposition cannot be pressed and calcined into mechanically stable particles of suitable size for fixed bed reactor use and maintain small metal crystallite size and high activity on a per unit of metal basis. For a discussion of calcination relative to pellet strength and catalyst activity see Satterfield, Heterogeneous Catalysis in Practice, Chemical Engineering Series, p. 75 and pp. 136–141, McGraw-Hill, Inc., 1980.

Another disadvantage of catalysts prepared by precipitation-deposition is that the active metal is distributed primarily on the outer circumference (in a sort of "egg shell" arrangement) of the catalyst particles (see e.g., U.S. Pat. No. 4,113,658 column 2, lines 10–14 and Augustine R. L., Heterogeneous catalysis for the Synthetic Chemist, p. 278, Marcel Dekker, Inc. (1996)).

Supported copper oxide crystallites, for example, those prepared according to the above discussed methods, can be converted to supported elemental copper crystallites by chemical reduction. Most commonly the elemental copper crystallites are obtained by reduction of the copper oxide crystallites with hydrogen at elevated temperatures (150 to 250° C.). A major problem in the art is that during reduction, sintering of the copper metal species can lead to increased metal crystallite size and consequently the resulting supported elemental copper catalyst has low catalytic activity on a per unit copper basis. Thus even if small copper oxide crystallites at high copper loading on the support are achieved, reduction to the elemental copper form generally results in a supported elemental copper catalyst of relatively low activity per unit copper metal.

In summary, the prior art has failed to disclose a supported copper catalyst characterized by small metal crystallite size, high active surface area, high mechanical stability (i.e., the aluminum oxide support is present in the γ-,δ-, θ-, or α-alumina phase), extended lifetime, high metal loading, and that is of particle size suitable for use in fixed bed type reactors. The prior art has also failed to disclose an aluminum oxide supported copper oxide catalyst, whereupon reduction affords a highly active aluminum oxide supported elemental copper catalyst characterized by high activity per unit metal. Such a catalyst would be especially useful for commercial hydration of nitriles to amides. These objectives are now fully met by the catalysts of the present invention as described below.

SUMMARY

The invention is directed to stable highly active supported copper based catalysts characterized by small crystallite size of the supported copper compound, high mechanical stability (i.e., pelletized γ-,δ-,θ-, or α-alumina or any mixture thereof, extended lifetime, high copper loading, and excellent resistance to hydration and copper leaching, and to methods for preparing the same. In a preferred embodiment, the catalyst is of a particle size suitable for use in fixed bed type reactors. The mechanically stable aluminum oxide support provides the catalyst with a long life time under vigorous reaction conditions, such as, those encountered during hydration reactions.

This invention also relates to a composition comprising small copper oxide crystallites supported on alumina that, upon reduction with hydrogen, yields an alumina supported elemental copper catalyst characterized by high activity per unit metal.

In one embodiment, the invention is directed to catalysts comprising crystallites of at least one copper compound deposited upon particles of γ-,δ-,θ-, or α-alumina or any mixture thereof, wherein the crystallites have an average crystallite size from about 20 to about 300 angstroms, the particles have an average diameter of from about 1 μm to about 20 mm, and the copper compound is present in an amount such that about 10 to about 35 weight percent of a total weight of the catalyst is copper metal.

Preferably the catalysts of the invention have a total surface area of from about 20 to about 400 square meters per gram. The catalyst particles of the invention are resistant to crushing and fragmentation.

In a further embodiment, the catalysts of the invention have total pore volume values (as measured by mercury porosimetry at 60,000 psi, a technique well known in the art) of about 0.5 to about 0.9 cc/g. Also, the total volume of the pores with diameter greater than 250 angstroms (as measured by mercury porosimetry), is preferably from about 0.1 to about 0.6 cc/g. In addition, catalysts of the invention preferably have a median pore diameter value, based on the surface area average, as measured by mercury porosimetry, from about 110 Å to about 340 Å.

The copper compound present as crystallites upon the surface of the alumina support may include cupric oxide (CuO), cuprous oxide ($CuO_2$), elemental copper ($Cu^0$), and any mixture thereof.

In further embodiments of the present invention, either of two metal deposition methods may be utilized to prepare stable, highly active, γ-,δ-,θ-, or α-alumina supported copper based catalysts, which methods—in contrast to the co-precipitation procedure discussed above—preclude copper occlusion within the support matrix. Thus, as prepared by these methods, the active component is more available for reaction and, therefore, has a higher activity per unit metal than co-precipitated type catalysts.

A first method for preparing the stable highly active supported copper catalysts of the invention includes the steps of:

(a) impregnating a mechanically stable phase of aluminum oxide with at least one chelating agent by contacting the aluminum oxide with a first solution, which first solution comprises a quantity of the chelating agent dissolved in a quantity of a first carrier liquid, to obtain aluminum oxide in a wetted pre-doped state;

(b) at least partially drying the wetted pre-doped aluminum oxide;

(c) impregnating the dried pre-doped aluminum oxide with at least one copper salt by contacting the pre-doped aluminum oxide with a second solution, which second solution comprises a quantity of the copper salt in a quantity of a second carrier liquid, to produce aluminum oxide in a wetted copper salt impregnated state;

(d) at least partially drying the wetted copper salt impregnated aluminum oxide; and (e) calcining the dried copper salt impregnated aluminum oxide to at least partially convert the impregnated copper salt to copper oxide crystallites.

A further embodiment of the invention comprises a second method for preparing the stable highly active supported copper catalysts of the invention, involving the steps of:

(a) impregnating a mechanically stable phase of aluminum oxide with at least one copper salt by contacting the aluminum oxide with a solution, which solution comprises a quantity of the copper salt and a quantity of ammonia at least partially dissolved in water, to produce aluminum oxide in a wetted copper salt impregnated state;

(b) at least partially drying the wetted copper salt impregnated aluminum oxide; and (c) calcining the dried copper salt impregnated aluminum oxide to at least partially convert the impregnated copper salt to copper oxide crystallites.

(d) If desired the catalyst as formed can be re-impregnated by repeating steps (a) through (c) one or more times.

The copper oxide crystallites, formed by the methods disclosed above, are preferably in the form of cupric oxide, cuprous oxide, or any mixture thereof.

In another embodiment, a stable active elemental copper based catalyst comprising mechanically stable aluminum oxide is prepared by repeating the steps of either of the methods described above and then, in a further step, at least partially reducing the copper oxide crystallites with at least one reducing agent, wherein at least a portion of the copper oxide crystallites are thereby converted to elemental copper crystallites.

Preferably, when the alumina supported copper oxide crystallites of the invention are reduced, the resulting alumina supported elemental copper catalyst is characterized by high catalytic activity per unit metal. Preferably the catalytic activity is such that during the hydration of acrylonitrile to acrylamide, in a fixed bed type reactor, the $k_{AN}$ value (defined as the rate of acrylonitrile disappearance in units of grams acrylonitrile feed/grams supported copper/min during the hydration of acrylonitrile performed according to the differential flow recycle microreactor hydration procedure described in Examples 4, 5, and 6 herein) measured is between about 0.5 to about 1.50.

Without wishing to be bound by theory, it is believed that the process used to make the alumina supported copper oxide catalysts of the invention, anchors the copper oxide crystallites to the alumina support in such a manner so as to prevent sintering during the reductive conversion to elemental copper crystallites. Thus, the integrity of the crystallites is maintained and the activity remains high. This is in contrast to prior art catalysts, whereupon reduction of the copper oxide crystallites is accompanied by sintering. Consequently, the reduced prior art catalyst is characterized by relatively large elemental copper crystallites (i.e., significantly larger than the starting copper oxide crystallites) and so the catalyst has a relatively low catalytic activity per unit copper metal manifested by low $k_{AN}$ values.

Chelating agents suitable for use in the first preparation method, include those known to form stable complexes with transition metals, especially with copper. Suitable first and second carrier liquids include those in which the chelating agents (first carrier liquid of the first method) and copper salt (both the first and second methods) is partially or fully soluble. Suitable carrier liquids are known and/or may be found by routine experimentation. Any copper salt that can bind to the aluminum oxide and that can subsequently be converted to copper oxide or elemental copper during calcination is suitable for either of the two methods. These copper salts are well known within the art and those preferred will depend on preparation factors, such as, the carrier liquid and the calcination temperatures.

A further embodiment of the invention comprises a process for at least partially hydrating a nitrile to an amide with the use of the catalysts of the invention. The process comprising the steps of selecting a catalyst, in accordance with the invention, loading a quantity of the catalyst and a mixture, the mixture comprising a quantity of water and a quantity of a nitrile, into a reactor and contacting the mixture and the catalyst therein in a manner and at a temperature effective to convert at least a portion of the nitrile into the amide, which conditions are well known in the art.

Advantageously, high stability and activity allows the presently disclosed and claimed catalysts to function continuously for extended periods in an aqueous medium (i.e., particularly in comparison to prior art catalysts) at an advantageous conversion rate and high selectivity. Processes for hydrating nitriles to amides with supported copper based catalysts are well known in the art. Some variations of this procedure are discussed in U.S. Pat. Nos. 3,994,973; 3,869,511; and 3,985,806 all of which are incorporated by reference herein. In a more preferred version, the nitrile is acrylonitrile and the amide is acrylamide. Use of the current invention, however, is not limited to hydration of nitriles. That is, the catalysts of the invention can also be used to catalyze many other reactions known to be mediated by copper catalysts. Examples of such reactions include, but are not limited to sulfur removal, xylene dimerization, alkyne dimerization, hydrogenation, NO removal, methanol synthesis, ester hydrogenolysis, amination, dehydroamination, oxidation, alkyl amine synthesis, disproportionation, cyclopropanation of olefins, and many others well known in the art.

These and other features, aspects, and advantages of the invention will become better understood with reference to the following detailed description and appended claims.

DETAILED DESCRIPTION OF THE INVENTION

The abbreviations, as used herein, are defined and measured as follows.

| Abbreviation | Definition |
| --- | --- |
| SA (nitrogen adsorption) | Total surface area, as measured in units of $m^2/g$ by nitrogen adsorption with an Autosorb-6B manufactured by Quantachrome Corp., Boynton Beach, Fl. A standard 7-point BET surface area analysis was used. |
| MPD (SA) | Median pore diameter, based on surface area average, as measured in units of angstroms by mercury porosimetry with an Autopore 9220 manufactured by Micromeritics Inc., Norcross Ga. A standard mercury porosimetry procedure with a contact angle of 140 degrees and a surface tension of 484 dyn/cm was used. |
| PV 60K | Total pore volume of a catalyst, as measured in units of cc/g by mercury porosimetry at 60,000 psi. |
| PV > 250 | Pore volume of a catalyst with pore diameter greater than 250 angstroms, as measured in units of cc/g by mercury porosimetry. |
| PV 60–10K | Incremental pore volume as measured by mercury porosimetry between 60,000 psi and 10,000 psi. |

The present invention is directed to stable highly active copper based catalyst particles comprising crystallites of at least one copper compound—preferably copper oxide or elemental copper—deposited upon a mechanically stable phase of aluminum oxide. The catalysts are characterized by an average crystallite size of the copper compound from about 20 Å to about 300 Å, a particle diameter of from about 1 μm to about 20 mm, and from about 10 to about 35 weight percent loading of the copper compound on a copper metal basis. As used herein, the term copper compound includes cupric oxide, cuprous oxide, elemental copper, or any mixture thereof. The catalysts preferably have a total surface area of from about 20 to about 400 square meters per gram.

In a preferred embodiment, the catalyst has an SA (nitrogen adsorption) of from about 80 $m^2/g$ to about 200 $m^2/g$, more preferably between about 90 $m^2/g$ and 100 $m^2/g$.

The copper compound's crystallite size is preferably from about 40 Å to about 130 Å, more preferably from about 50 Å to about 100 Å.

Preferably the catalyst particles have an average diameter of from about 0.1 mm to about 10 mm, more preferably from about 1 mm to about 5 mm, and optimally about 2 mm to about 3 mm.

In another preferred embodiment, the copper compound is present in an amount such that from about 15 to about 25 weight percent of a total weight of the catalyst is copper, more preferably from about 18 to about 22 weight percent is copper.

In a further embodiment, the catalysts of the invention preferably have PV 60K values of about 0.5 cc/g to about 0.9 cc/g, more preferably about 0.6 cc/g to about 0.8 cc/g, and most preferred about 0.65 cc/g to about 0.7 cc/g.

In addition, the catalysts preferably have PV>250 Å values of about 0.1 cc/g to about 0.6 cc/g, more preferably from about 0.2 cc/g to 0.4 cc/g, and most preferably from about 0.25 cc/g to 0.3 cc/g.

Still further, the catalysts of the invention preferably have MPD (SA) values of about 110 Å to about 340 Å, more preferably about 180 Å to about 280 Å. The most preferred range is about 205 Å to 235 Å.

In yet another embodiment of the invention, when the alumina supported copper oxide crystallites of the invention are reduced with hydrogen at elevated temperature, the resulting alumina supported elemental copper catalyst of the invention is characterized by high catalytic activity per unit metal.

Preferably the catalyst has an activity such that a $k_{AN}$ value measured for an acrylonitrile hydration reaction performed with said catalyst is about 0.7 to about 1.3, more preferably about 0.9 to about 1.2. The preferred reducing agent is hydrogen and the reduction is preferably carried out at elevated temperature, preferably from about 300° C. to about 500° C., more preferably from about 100° C. to about 250° C.

As noted above, the mechanically stable forms of aluminum oxide useful for preparation of the catalysts of the invention include γ-, δ-, θ-, and α-alumina, and any mixture thereof. While α-alumina is preferred for acrylonitrile hydration, the other stable aluminum oxide phases have inherent advantages that may make them preferred catalyst supports for other chemical transformations, such as: sulfur removal, xylene dimerization, alkyne dimerization, hydrogenation, NO removal, methanol synthesis, ester hydrogenolysis, amination, dehydroamination, oxidation, alkyl amine synthesis, disproportionation, cyclopropanation of olefins and many others. The γ-alumina may be purchased, for example, from the Criterion Catalyst Company (Houston, Tex.), while the other above mentioned mechanically stable aluminum oxide phases may be prepared by methods well known to those of ordinary skill in the art.

The present invention will work with any calcined crystalline aluminum oxide substrate, although Wide Pore Alumina (WPA powder, The Criterion Catalyst Company, Houston, Tex.) is preferred. WPA powder has a PV 60–10K of about 0.84 cc/g; a median pore diameter (SA) of about 97 Å; and a loss on ignition of about 27 weight percent.

The mechanically stable aluminum oxide support substrates can be prepared by mixing an initial phase of aluminum oxide, preferably bauxite in the form of boehmite aluminum oxide (AlO(OH)) or Criterion Wide Pore Alumina, with water, extruding the hydrated aluminum oxide/water through a die in a suitable form (the die defines the shape of the extruded aluminum oxide); at least partially drying the extruded aluminum oxide; and calcining the dried extruded aluminum oxide at a temperature sufficient to convert the hydrated aluminum oxide to the mechanically stable phase of aluminum oxide. This and similar methods are well known in the art, for example see: *The Encyclopedia of Chemical Technology*, 2 Kirk-Othomer ($4^{th}$ ed. at 291–330), incorporated herein by reference.

The shape of the extruded aluminum oxide is not particularly important for practice of the invention. The inventors have found that a standard ⅛ inch cylindrical die (Criterion Catalyst Company, Houston, Tex.) works well for shaping the aluminum oxide during extrusion. Also preferred is a 2.7 mm Trilobe® die. The 2.7 mm Trilobe die is similar in all respects to the standard commercial dies for making aluminum oxide catalyst extrudates. The 2.7 mm Trilobe extrudate resembles a three leaf clover-shape (2.7 mm is the diameter of a imaginary circle just encompassing the clover shape).

The dried extrudate can be calcined according to the following temperatures for about 0.5 to about 1.5 hours, depending on the mechanically stable aluminum oxide phase desired.

γ-alumina: at about 550° C. to about 850° C.
δ-alumina: at about 875° C. to about 1000° C.
θ-alumina: at about 950° C. to about 1050° C.
α-alumina: over about 1100° C.

Advantageously, the extruded calcined aluminum oxide support should have a surface area in the range of about 5 $m^2/g$ to about 400 $m^2/g$, preferably about 100 $m^2/g$ to about 200 $m^2/g$, more preferably about 135 $m^2/g$ to about 145 $m^2/g$. As discussed above, the aluminum oxide support surface area depends upon the calcination temperature. Generally, γ-alumina, prepared by calcination of boelimite at 550° C. to about 850° C., has a surface area of about 50 to 300 $m^2/g$. Upon further calcination, to effect the transition from γ- through δ-and θ- to α-alumina, the surface area will decrease to as low as 5 $m^2/g$. The preferred support, θ-alumina, has a surface area of about 130 to 150 $m^2/g$.

Also, the extruded calcined aluminum oxide support should have a PV 60K in the range of about 0.5 cc/g to about 1.6 cc/g, preferably about 0.9 cc/g to about 1.3 cc/g, more preferably about 1.0 cc/g to about 1.2 cc/g.

In addition, the extruded calcined support should have a PV>250 Å in the range of about 0.3 cc/g to about 0.8 cc/g, preferably about 0.4 cc/g to about 0.6 cc/g, more referably about 0.45 cc/g to about 0.55 cc/g.

Still further, the extruded calcined support should have a MPD (SA) in the range of about 110 Å to about 290 Å, preferably about 160 Å to about 220 Å, more preferably about 180 Å to about 210 Å.

Although the support is preferably aluminum oxide, other well known support materials, such as, silica, silica/alumina mixtures, carbon, zeolites, kieselguhr, pumice, diatomaceous earth, activated carbon, and titania, as well as others known to those of ordinary skill in the art, may also be used.

When the first of the preparation methods described above is utilized, some exemplary chelating agents include, but are not limited to, ethylenediaminetetraacetic acid and its homologs; tris(2-aminoethyl)amine; triethylenetetraamine; diethylenetriaminepentaacetic acid; 1,2-diaminoeyclohexane-N,N,N',N'-tetraacetic acid, ethylene glycol bis(2-aminoethylether)-N,N,N',N'-tetraacetic acid; tetraethylenepentaamine; as well as any of the salts of these materials. Particularly preferred chelating agents are the salts of ethylenediaminetetraacetic acid, especially ethylenediaminetetraacetic acid diammonium salt (DA-EDTA); ethylenediaminetetraacetic acid, dipotassium salt; and ethylenediaminetetraacetic acid, disodium salt.

The suitability of other chelating agents can readily be determined by those of ordinary skill in this art by performing the steps of the first disclosed catalyst forming process with the chelating agent in question. Then, it is a simple matter to determine whether the catalyst thus formed is characterized by an average crystallite size of the copper compound from about 20 to about 300 angstroms and copper loading of about 10 to about 35 weight percent on a copper metal basis.

The most preferred first carrier liquid for use with the first process for forming the catalysts of the invention is water.

The particular chelating agent concentration in the carrier liquid is not critical and can be varied depending on its solubility in the carrier liquid, the identity of the copper salt to be subsequently impregnated, and the degree of impregnation desired. For example, if the chelating agent is DA-EDTA, the carrier liquid is preferably water and the amount of DA-EDTA relative to the aluminum oxide can be in the range of about 0.1 to about 0.3 g/g aluminum oxide, preferably from about 0.15 to about 0.25 g/g aluminum oxide, more preferably from about 0.18 to about 0.22 g/g aluminum oxide, most preferably 0.19 to 0.21 g/g aluminum oxide.

The aluminum oxide can be contacted with the chelating agent-carrier liquid composition by any known method, which methods are well known to those of ordinary skill in the art, such as pore-volume impregnation (PVI). Pore volume impregnation involves saturating or filling all the pore volume with liquid. Pore volume impregnation can be accomplished, e.g., on a lab scale, by placing a quantity of calcined aluminum oxide substrate in a standard wide-mouth glass bottle at room temperature, and adding the impregnating solution while gently shaking the bottle until the aluminum oxide substrate is saturated, as evidenced by slight sticking of the particles. The bottle is capped, and the impregnating solution is distributed uniformly within the internal pores of the aluminum oxide by rolling or shaking the sample bottle, for about 10 to about 15 minutes.

The wetted pre-doped aluminum oxide can be dried by conventional methods well known to those of ordinary skill in the art. Air drying is preferred. The preferred air drying temperature is about 150° C. to about 205° C. for about 0.5 to about 2 hours, preferably from about 160° C. to about 190° C. for about 0.75 to about 1 hour.

A variety of copper salts for use in the first and second catalyst preparation methods described herein are within the scope of the invention and a few non-limiting examples are cited here. These include copper salts having nitrogen-containing anions such as copper nitrate, copper nitrite, copper nitride, copper cyanide, copper ferrocyanide; copper salts having halogen-containing anions, such as copper chloride, copper bromide, copper perchlorate, copper bromate, and copper iodide; copper salts having sulfur containing anions, such as, copper sulfide, copper sulfate, and copper thiocyanate; copper salts having organic carboxylic acid containing anions, such as copper carbonate, copper formate, copper acetate, copper oxalate, copper butyrate, copper citrate, copper benzoate; and other copper salts such as copper borate, copper phosphate, copper carbide, copper chromate, and copper tungstate. The preferred copper salts are copper nitrate and copper formate with copper nitrate more preferred for the first of the two disclosed methods and copper formate more preferred for the second.

The second carrier liquid for use in forming the catalysts of the invention is preferably water, but any carrier liquid in which the copper salt is partially or fully soluble is within the invention's scope.

In the second method described herein, no particular ammonia concentration limit is contemplated. An exemplary concentration is about 1 to about 47 weight percent, more preferably about 25 to about 34 weight percent.

The copper salt concentration employed in the methods of the invention is not critical and will vary in a manner well understood by those of ordinary skill in the art, depending on the copper salt's identity, its solubility, and the degree of impregnation desired. For example, in the first method, if aqueous copper nitrate is used, the concentration is ideally from about 12 to about 25 weight percent, preferably from about 18 to about 20 weight percent. In the second method, if the salt is copper formate, the concentration is preferably from about 5 to about 20 weight percent, more preferably from about 13 to about 14 weight percent.

The dried pre-doped aluminum oxide can be contacted with the copper salt-carrier liquid by methods well known to those of ordinary skill in the art, for example, the pore-volume impregnation (PVI) method described above.

In both of the two methods described herein for forming the catalyst, after impregnation of the aluminum oxide with a copper salt, the copper salt impregnated aluminum oxide can be dried by conventional methods. Air drying is preferred. The preferred air drying temperature is about 150° C. to about 205° C. for about 0.5 to about 2 hours, preferably from about 160° C. to about 190° C. for about 0.75 to about 1 hours.

Calcining the dried, copper salt impregnated aluminum oxide—derived from either the first or second catalyst forming methods of the invention—to convert the impregnated copper salt to copper oxide, and thus arrive at the supported copper oxide catalyst composition, is conducted at a temperature sufficient to convert the supported copper salt to copper oxide crystallites. During the calcination, the copper salt is preferably converted to cupric oxide, cuprous oxide, or a mixture of the two. The calcination temperature is readily determined by one of ordinary skill in the art and will vary depending on the identity of the copper salt and its decomposition temperature. Preferably a maximum temperature is used, which will not cause sintering of the supported copper. In general the calcination temperature will range from about 200° C. to about 600° C. for about 30 minutes to about 2 hours. For example, if the copper salt is copper nitrate, the preferred calcination temperature is the range of about 250° C. to about 540° C. for about 30 minutes to 120 minutes, even more preferably from about 390° C. to about 410° C. for about 45 to 75 minutes. If the copper salt is copper formate, the preferred calcination temperature ranges from about 350° C. to about 450° C. for about 30 minutes to about 120 minutes, even more preferably from about 390° C. to about 410° C. for about 45 minutes to about 75 minutes.

Calcination procedures and apparatuses are well known within the art. Conventional ovens, rotary kilns, stationary or fluid bed calciners, and fluid-flash calciners have been used for many years.

In a further embodiment, a catalyst may be prepared by following either the first or the second methods described above, and then, subsequently, at least partially reducing the supported copper oxide crystallites to a catalyst comprising elemental copper crystallites supported on the mechanically stable aluminum oxide. The reduction can be carried out in the liquid or gas phase. A variety of reducing agents, well known to those of ordinary skill in the art, are suitable for use with the invention, for example, carbon monoxide, ammonia, a lower alkane, a lower alkanol, hydrazine, a hypophosphite, and hydride reducing agents such as sodium borohydride and lithium aluminum hydride. Some additional reducing agents are listed in Hudlicky M. Reductions in Organic Chemistry, ACS Monograph 188, American Chemical Society, Washington D.C., 1996, incorporated herein by reference. The preferred reducing agent is hydrogen.

Hydrogen reduction of copper oxide supported on aluminum oxide is well known in the art. Exemplary procedures are described in U.S. Pat. Nos. 4,493,906; 4,234,727; 3,758,578; and 3,631,104; and EP 434,061 B1 and EP 695,579 A1, all of which are incorporated by reference herein.

It is also well known in the art to adjust the interrelationship of temperature, reaction time, and hydrogen pressure to obtain the desired degree of catalyst activity. The reduction temperature is generally in the range of from about 10° C. to about 300° C., preferably in the range of from about 100° C. to about 250 ° C. The reduction time is preferably in the range of from about one minute to about 30 hours, more particularly from about 10 minutes to about 15 hours. Upon such reduction, the copper oxide crystallites are partially or fully converted to elemental copper. The reduction reaction may be monitored and controlled by methods well known in the art, such as, measuring the quantity of reducing agent reacted, the amount of by-product formed, or the weight loss incurred by the supported copper oxide composition. The degree of reduction may be determined by x-ray diffraction or elemental analysis in a manner well known in the art.

The copper based catalyst compositions of the invention are useful, for example, for hydrating nitriles. Processes for hydrating nitrites to amides with supported copper based catalysts are well known in the art. Some variations of this procedure are described in U.S. Pat. Nos. 3,994,973; 3,869, 511; and 3,985,806, all of which are incorporated herein by reference. Catalysts of the invention can be used in these processes or variations thereof.

Nitriles containing one to about twenty carbons are the preferred substrates for the hydration reaction. Representative examples of suitable nitrites include but are not limited to: saturated aliphatic hydrocarbon nitrites, such as, acetonitrile, propionitrile, pentanonitrile, dodecanonitrile, adiponitrile and the like; and unsaturated aliphatic hydrocarbon nitriles, such as, acrylonitrile, methacrylonitrile, crotonic nitrite, β-phenylacrylonitrile, 2-cyano-2-butene, 1-cyano-1-octene, 10-undecenonitrile, maleonitrile, fumaronitrile. Of the nitriles suitable for use in the current invention, the olefinic nitriles of three to six carbon atoms are especially preferred, with the conversion of acrylonitrile to acrylamide being of particular interest.

No particular restriction is imposed on the amount of the water used in the hydration reaction, but excess water is preferred. The optimum concentration of nitrite will vary depending on the nitrite identity and the reaction conditions. Optimum concentrations can be determined by routine experimentation. For acrylonitrile, the weight percent of nitrite is preferably from about 1 to about 50%, more preferably from about 3 to about 10%, and optimally from about 5 to about 6%. Although not required, the water and nitrite may be mixed to promote reaction efficiency. The mixing may be carried out by dissolving the nitrile in the water with or without agitation. When the nitrite is not fully dissolved, other steps may be taken to ensure intimate nitrile/water mixing. For example, a biphasic mixture may be agitated or a suitable solvent may be added to enhance the nitrile's solubility in the aqueous phase. While excess water is the preferred solvent, as noted above, alternate inert solvents, such as, alkanols, dioxane, diethyl sulfoxide, acetone, dimethyl ether of ethylene glycol, or tetrhydrofuran, may be used. The pH is not a critical factor but generally neutral or slightly acidic conditions are used.

The catalyst compositions of the invention can be used in both batch and continuous flow hydrations. Using either method, the nitrile and water are contacted with the catalyst under the appropriate reaction conditions, and the amide product is then recovered. Since these catalysts are essentially insoluble, a continuous flow reaction is preferred. If the conversion of nitrile to amide is incomplete, the nitrile can be separated from the amide by conventional methods, well known in the art, such as distillation. The amount of the present catalyst required to effect a particular chemical transformation is relative to the substrate, the degree of conversion desired, the dimensions and type of reactor, and the reaction conditions. One of ordinary skill in the art can readily determine the optimal catalyst amount by routine experimentation.

In a continuous flow reaction, the solid catalyst is packed into a reaction chamber having an inlet for reactants and an outlet for products. The reaction chamber is maintained at the desired reaction temperature and the flow rate of reactants over the catalyst is controlled to give the desired conversion degree of nitrile to amide. The reaction can be performed with contact times from about 1 to about 20 minutes. The reactants may be fed over the catalyst as a gas or preferably as a liquid.

The temperature of the reaction may vary widely depending on the nitrile to be hydrated. Generally the reaction is conducted at from about room temperature to about 400° C. At lower temperatures, the reaction is impractically slow. Above this preferred range, the reaction produces an increasing amount of by-products. When operating in the liquid phase, temperatures of about 25° C. to about 200° C. are preferred. For unsaturated nitrites which tend to polymerize, a reaction temperature of less than about 200° C. is preferred. For acrylonitrile a temperature in the range of about 90° C. to about 130° C. is preferred. Polymerization inhibitors can be added to the acrylonitrile feed or dilute reaction conditions can be employed to prevent nitrile polymerization. The other reaction conditions are well known in the art of using heterogeneous catalysts and are not critical in the invention. The reaction product from the reactor may be purified by any conventional technique, such as distillation or recrystallization. The unreacted nitrile can be separated and recycled according to conventional techniques.

The catalysts of the invention have many advantages over the prior art catalysts. The combined characteristics of high surface area and small crystallites in conjunction with high metal loading and mechanically stable aluminum oxide support phases, renders these catalysts highly active and stable, with high resistance to hydration, copper leaching, and fragmentation. Prior art aluminum oxide based catalysts are vulnerable to deactivation under aqueous phase reaction conditions. The catalysts of the current invention are highly stable under aqueous conditions and are well suited for hydration reactions.

Furthermore, the current catalysts are prepared by a method that precludes entrapment of the copper within the support matrix, and as such, have much higher activity per unit metal than co-precipitated type catalysts. In addition, since the catalysts of the invention are supported on extruded calcined aluminum oxide, the cumbersome pelletization step, required for the co-precipitated catalysts, is not necessary.

Although the present invention has been described in considerable detail with reference to certain preferred embodiments, other embodiments are possible. Therefore, the spirit and scope of the appended claims should not be limited to the description of the preferred embodiments contained herein.

EXAMPLES

The following examples are provided for illustrative purposes only and are not to be construed as limiting the invention's scope in any manner.

Example 1

This Example describes a preparation of a mechanically stable θ-alumina support.

A muller was charged with 5.4 pounds of Wide Pore Alumina powder containing 20 dry weight % fines (available from Criterion Catalyst Company (Houston, Tex.)). Deionized water was added to form a slurry mixture, wherein the mull solids were 35 weight percent of the total mixture. No acid or ammonia was used in the muller formulation. The mixture was mulled for 15 minutes at room temperature then extruded using 2.7 mm Trilobe die (Criterion Catalyst Company, Houston Tex.). The extruded alumina was dried for 3 hours at 110° C. in a lab convection oven. The extruded alumina was calcined under an atmosphere containing about 15 weight percent water vapor at 1000° C. for 90 minutes in a lab quartz tube furnace. The calcined substrate had the following properties:

| Aluminum oxide phase | θ-alumina | PV 60K | 1.12 cc/g |
|---|---|---|---|
| SA (nitrogen adsorption) | 139 m²g | PV < 250 Å | 0.50 cc/g |
| | | MPD (SA) | 193 Å |

Example 2

This Example describes the preparation of a mechanically stable copper oxide catalyst supported on the θ-alumina of Example 1.

The θ-alumina (705 g), prepared in Example 1 was impregnated with a solution of ethylenediaminetetraacetic acid, diammonium salt (DA-EDTA) at 100% of pore volume (i.e., the quantity of solution required to substantially fill the available pore volume). The alumina was placed in a standard wide-mouth glass bottle (1 gal) and aqueous ethylenediamine-tetraacetic acid, diammonium salt (0.6 M) was added with gentle shaking until the aluminum oxide was saturated as evidenced by slight sticking of the particles. The bottle was capped, and the impregnating solution was distributed uniformly by rolling the bottle, for about 10 to 15 minutes. The impregnate was allowed to stand in the capped bottle for two hours at ambient temperature, then dried in a forced air oven at 175° C. for 45 minutes.

The pre-doped substrate, as prepared above, was impregnated in the sample jar at 100% of pore volume by adding aqueous copper nitrate solution (specific gravity=1.68) (1.67 M) with gentle shaking until the aluminum oxide was saturated as evidenced by slight sticking of the particles. The bottle was capped, and the impregnating solution was distributed uniformly by rolling the sample bottle for about 10 to 15 minutes. The impregnate was allowed to stand in the sealed bottle for two hours at ambient temperature, and dried and calcined in a muffle furnace at 250° C. for 20 minutes; 400° C. for 20 minutes; and 540° C. for 20 minutes. The finished catalyst had the following properties:

| Aluminum oxide phase | θ-alumina | PV 60K | 0.67 cc/g |
|---|---|---|---|
| Cu wt % | 20.2% | PV > 250 Å | 0.28 cc/g |
| XRD CuO crystallite size | 98 Å | MPD (SA) | 220 Å |
| SA (nitrogen adsorption) | 95 m²/g | | |

Example 3

This Example describes the preparation of a mechanically stable copper oxide catalyst supported on γ-alumina.

Wide pore γ-alumina (20 g) was placed in a standard wide-mouth glass bottle (130 ml) and 13.6 weight% copper formate in concentrated aqueous ammonia (30%) was added with gentle shaking until the aluminum oxide was saturated as evidenced by slight sticking of the particles. The bottle was capped, and the impregnating solution was distributed uniformly by rolling the sample bottle, for about 10 to 15 minutes. The impregnate was allowed to stand in the sealed bottle for two hours at ambient temperature, then dried in a fluid bed drier (available from Lab-Line Instruments Inc., Melrose Park, Ill. 60160) at 175° C. for 10 minutes, and calcined in a muffle furnace at 400° C. for 60 minutes.

The impregnated substrate was impregnated again, by repeating the above procedure. The resultant catalyst had the following properties.

| Aluminum oxide phase | γ-alumina |
|---|---|
| Cu wt % | 26% |
| XRD CuO crystallite size | 74 Å |

Example 4

This example describes the formation of a mechanically stable elemental copper based catalyst comprised of elemental copper supported on θ-alumina.

The Example 2 catalyst (5 g) was loaded into a fixed bed differential flow recycle microreactor designed to measure catalyst activities. The reactor was comprised of a reactor tube (3 inch by ⅜ inch OD (wall thickness=0.35 inch) stainless steel tube) packed with the catalyst, thus forming a fixed reactor bed. Stainless steel screens were used to hold the catalyst firmly within the reactor body. Thermocouples were used to measure the reactor body inlet and exit temperatures. The fixed bed was immersed in a fluidized-bed sand bath (Techne Corporation, Princeton N.J. 08540), which provided uniform heating of the reactor contents. The sand bath was charged with aluminum oxide powder, which was used as a heating medium. Air was charged to a perforated plate at the bottom of the sand bath to provide fluidization to the heating bath, and electric heating coils provided heat to the aluminum oxide powder.

A feed system was designed to allow reduction or partial reduction of the supported copper oxide to elemental copper in situ using hydrogen flow. The reduction was begun at 0.5% hydrogen in nitrogen at a flow rate of 200 std. cm³/minute and 160 ° C. The temperature and hydrogen concentration were gradually increased to about 225° C. and about 100% hydrogen at a flow rate of 300 cm³/minute over a period of 2 hours. The hydrogen flow was then stopped and the reactor was allowed to cool to room temperature, while increasing the nitrogen flow to 200 cm³/min.

Example 5

This example describes a hydration of acrylonitrile to acrylamide—according to a differential flow recycle microreactor hydration procedure—using the mechanically stable elemental copper based catalyst of Example 4.

The elemental copper based catalyst and the differential flow recycle microreactor as described in Example 4 above were used. The hydration was run under an oxygen free atmosphere to avoid oxidizing the elemental copper catalyst. The catalyst, as prepared in the reactor tube of Example 4, was purged with nitrogen, then wetted by pumping deacrated, distilled water over the catalyst at approximately 5 cc/min. for about 1 hour.

The reactor was connected to a positive displacement pump providing recycle flow over the catalyst bed at about 100 g/min. The reactor was maintained at 100° C. and nitrogen purged acrylonitrile (5.7 weight percent aqueous solution) was then charged to the reactor tube at about 4 g/min. The recycle flow was used to provide high fluid velocities (about 100 cc/min) over the catalyst particles, to minimize potential external particle mass transfer resistances on the reaction rate. Conversions were up to 30% and the selectivity was 99%.

Example 6

This example compares acrylonitrile hydration activities of the current catalysts with the hydration activity of the prior art co-precipitated Calsicat®, catalyst No. X-415, which is commercially available (Engelhard Corp. Chardon, Ohio) copper oxide catalyst supported on aluminum oxide. Calsicat X-415 is prepared by co-precipitation of copper salts and aluminum salts, contains about 47 weight percent copper as copper oxide, and has an average copper oxide crystallite size of about 120 Å.

The hydration reactions were performed using differential flow recycle microreactor hydration procedure described in Examples 4 and 5 above. In Run 1, Calsicat X-415, was used to hydrate acrylonitrile, while in each of Runs 2–6 (see Table 1 below), a sample of a catalyst produced according to the invention was used.

For each run, the catalyst was loaded into the fixed bed differential flow recycle microreactor (described in Example 4) and the system was pressure tested. The catalyst was dried overnight under nitrogen, at ambient temperature. The copper oxide catalyst was reduced—as in Example 4—by maintaining the reactor at 160° C. while purging hydrogen, diluted to about 0.5% with $N_2$, through the catalyst at a flow rate of 150 std. $cm^3$/minute. The hydrogen concentration was increased step-wise to 100% while increasing the reactor bed to 225° C. over 2 hours to complete reduction of the catalyst in situ.

The catalyst, as reduced above, was purged with nitrogen, then wetted by pumping deaerated, distilled water over the catalyst at approximately 5 cc/min.

The reactor was connected to a positive displacement pump providing recycle flow over the catalyst bed at about 100 g/min. The reactor was maintained at 100° C. and nitrogen purged acrylonitrile (5.7 weight percent aqueous solution) was then charged to the reactor tube at about 4 g/min.

About 8 to 12 effluent samples were collected during the hydration at 15 minute intervals, analyzed for acrylonitrile and acrylamide content by gas chromatography to ensure the system had reached a steady state.

For each sample a $k_{AN}$ [first order rate of acrylonitrile disappearance in units of grams feed/grams Cu/min] was calculated. The rate constant $k_{AN}$ was calculated according to the equation below.

$$k_{AN} = F^\circ / W_{cat}[X_{AN}/(1-X_{AN})]$$

where:

$F^\circ$ = feed rate of the 5.7% aqueous acrylonitrile (g/min)
$W_{cat}$ = catalyst weight per gram supported copper metal (g)
$X_{AN}$ = conversion of acrylonitrile into acrylamide from the reactor inlet to the outlet The relationship for calculating the first-order rate constant was derived by assuming first-order kinetics for acrylonitrile disappearance (pseudo-zero-order in water concentration) and writing appropriate mass balances. The conversion across the catalyst itself was differential, i.e., the reactor tube could be considered a perfectly back-mixed continuous-stirred-reactor-tank, again due to the high recycle rates and small catalyst masses used. Therefore, the mass balance equations could be written algebraically, and the first-order rate constant calculated from Equation 1 by reducing the set of algebraic equations formed.

The hydration reaction was stopped by discontinuing acrylonitrile/water feed and switching to deaerated water to flush the system. Finally, the system was purged overnight with nitrogen to dry the catalyst and flush the system. The catalyst activity data is presented in Table 1, below.

TABLE 1

| Run | Catalysts | temperature at which the alumina support was calcined | wt % CuO | CuO crystallite size | $k_{AN}$ |
|---|---|---|---|---|---|
| 1 | Calsicat X-415 amorphous alumina | Formed by co-precipitation. | 47% | 120 Å | 0.50 |
| 2 | CuO on γ-alumina extruded as a 2.7 mm Trilobe | 800° C. | 22% | 73 Å | 0.87 |
| 3 | CuO on biphasic mixture of γ-, and θ-alumina extruded as 2.7 mm Trilobe | 950° C. | 23% | 60 Å | 0.94 |
| 4 | CuO on θ-alumina extruded as 2.7 mm Trilobe | 1000° C. | 20% | 91 Å | 1.12 |
| 5 | CuO on θ-alumina extruded as 2.7 mm Trilobe | 1000° C. | 20% | 72 Å | 1.19 |
| 6 | CuO on biphasic mixture of θ-, and α-alumina extruded as 2.7 mm Trilobe | 1050° C. | 21% | 83 Å | 0.78 |

The data presented in Table 1 demonstrates that the acrylonitrile hydration activity per unit copper metal of the invention's catalysts—as measured by the first order rate constant for acrylonitrile hydration ($k_{AN}$)—is about 1.5 to about 2.4 times more active than the prior art catalyst, Calsicat X-415, on a per unit mass of copper basis.

Example 7

This example demonstrates the improved resistance to re-hydration of the catalysts of the invention compared to currently available aluminum oxide supported copper catalysts.

An aqueous solution of acrylonitrile and acrylamide (25 ml; 5.0% acrylonitrile and 1.0% acrylamide, stabilized with 0.1% methylhydroquinone, Aldrich) was charged to a 37 ml pressure vessel (manufactured by Pressure Products Industries Inc., Warminister, Pa.) containing a copper on aluminum oxide catalyst. In each of Runs 1–3, a catalyst of the invention was used, while, in Run 4, the prior art catalyst Calsicat X-415 was used (see Table 2 below). The pressure vessel was sealed under ambient atmosphere and heated to 120° C. in a convection oven without agitation, wherein the pressure rose to about 60 psig. After 11 days, the pH of the resulting mixture was measured, and the degree of re-hydration of the aluminum oxide component of each sample was estimated by X-ray diffraction spectroscopy, using the integrated intensities of the boehmite peak to the θ-alumina peak.

TABLE 2

| Run | Catalyst/ alumina phase | Calcination temperature | wt % CuO | CuO crystallite size | pH | Degree of rehydration |
|---|---|---|---|---|---|---|
| 1 | CuO on biphasic mixture of γ-, and θ-alumina ex- | 950° C. | 23 | 60 Å | 7.3 | 36% |

TABLE 2-continued

| Run | Catalyst/ alumina phase | Calcination temperature | wt % CuO | CuO crystallite size | pH | Degree of rehydration |
|---|---|---|---|---|---|---|
| | truded as 2.7 mm Trilobe | | | | | |
| 2 | CuO on θ-alumina extruded as 2.7 mm Trilobe | 1000° C. | 20 | 71 Å | 7.5 | 21% |
| 3 | CuO on biphasic mixture of θ-, and α-alumina extruded as 2.7 mm Trilobe | 1050° C. | 21 | 83 Å | 7.7 | 12% |
| 4 | Calsicat X-415 | about 550° C. | 47% | 120 Å | 7.2 | 100% |

The catalysts of Runs 1,2, and 3—prepared according to the teachings of the invention—demonstrated superior water reabsorption resistance in comparison to the prior art catalyst, Calsicat X-415 of (Run 4).

Example 8

This example demonstrates the superior copper leaching resistance of a catalyst of the invention over prior art aluminum oxide supported copper based catalysts.

During the hydration of acrylonitrile—according to the procedure described in Examples 4 and 5 above—the copper content in the reactor effluent was measured at 24 hour intervals to obtain comparative copper leaching values for both a catalyst of the invention [24% by weight copper on ⅛" γ-alumina cylinders with an average copper compound crystallite size of 96 Å] and the prior art catalyst, BASF R3-18 (BASF, Edison, N.J.). BASF R3-18 is a co-precipitated copper oxide on aluminum oxide catalyst with an average copper oxide crystallite size of about 50 Å and copper loading of about 50%, which is similar to Calsicat X-415. The reactor was operated in a once-through mode, with no recycle and three discrete fixed catalyst beds (14 inches by 1.5 inches ID) were employed as the reaction path. The beds operated in series with the effluent from the first bed feeding the second (combining with fresh acrylonitrile solution at the inlet), and so forth.

For each of the two catalysts, the once-through reactor was charged with about 1600 g of catalyst and a 5.7% aqueous solution of acrylonitrile was charged to each bed at a rate of 4 gallons per day at a reactor exit temperature of 115° C. Four ounce reactor effluent aliquots were removed every 24 hours and the copper concentration in ppm was measured by colorimetry with Cuprizon-1 (oxalic bis (cyclohexylidenehydrazide, Aldrich). The comparative data obtained for the catalyst of the invention versus the prior art catalyst, BASF-R3-18, is shown in Table 3 below.

TABLE 3

| Prior art catalyst BASF R3-18 | | Catalyst of the invention | |
|---|---|---|---|
| Sample No. | Cu ppm | Sample No. | Cu ppm |
| 1 | 102 | 1 | 118 |
| 2 | 100 | 2 | 60 |
| 3 | 136 | 3 | 22 |
| 4 | 103 | 4 | 19 |
| 5 | 80 | 5 | 10 |
| 6 | 62 | 6 | 13 |
| 7 | 60 | 7 | —* |
| 8 | 56 | 8 | 13 |
| 9 | 46 | 9 | —* |
| 10 | 36 | 10 | 13 |
| 11 | 34 | 11 | 13 |
| 12 | 30 | 12 | 8 |
| 13 | 29 | 13 | 18 |

*No measurement was obtained at this time interval.

Thus, the copper leaching values in Table 3 above demonstrate that the catalyst of the invention has superior resistance to copper leaching, over the prior art catalyst, BASF R3-18, during the hydration of acrylonitrile.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

What is claimed is:

1. A catalyst comprising crystallites of at least one copper compound deposited upon particles of a mechanically stable phase of aluminum oxide, wherein the crystallites have an average size of from about 20 to about 300 angstroms, the particles have an average diameter of from about 1 $\mu$m to about 20 mm, and wherein about 10 to about 35 weight percent of a total weight of the catalyst is copper metal.

2. The catalyst of claim 1, wherein the mechanically stable phase of aluminum oxide is γ-alumina, δ-alumina, θ-alumina, α-alumina, or a mixture thereof.

3. The catalyst of claim 1, wherein the catalyst has a total surface area from about 20 to about 400 square meters per gram.

4. The catalyst of claim 1, wherein the average crystallite size is from about 40 to about 130 angstroms.

5. The catalyst of claim 1, wherein the particles have an average diameter of from about 0.1 mm to about 10 mm.

6. The catalyst of claim 1, wherein the copper compound is present in an amount such that from about 15 to about 25 weight percent of the total weight of the catalyst is copper.

7. The catalyst of claim 1, wherein the catalyst has a total pore volume, as measured by mercury porosimetry at 60,000 psi, from about 0.5 to about 0.9 cc/g.

8. The catalyst of claim 1, wherein the total volume of pores with diameter greater than 250 angstroms in said aluminum oxide is from about 0.1 to about 0.6 cc/g.

9. The catalyst of claim 1, wherein the catalyst has a median pore diameter, based on an average surface area thereof, from about 110 to about 340 angstroms.

10. The catalyst of claim 1, wherein the copper compound is cupric oxide, cuprous oxide, or a mixture thereof.

11. The catalyst of claim 1, wherein at least a portion of the copper compound is elemental copper.

12. The catalyst of claim 1, wherein the mechanically stable phase of aluminum oxide is θ-alumina.

13. A method of preparing a catalyst, said method comprising the steps of:

(a) impregnating a mechanically stable phase of aluminum oxide with at least one chelating agent by contacting the aluminum oxide with a first solution, which first solution comprises a quantity of the at least one chelating agent dissolved in a quantity of a first carrier liquid, to obtain aluminum oxide in a wetted pre-doped state;

(b) at least partially drying the wetted pre-doped aluminum oxide;

(c) impregnating the dried pre-doped aluminum oxide with at least one copper salt by contacting the pre-doped aluminum oxide with a second solution, which second solution comprises a quantity of the copper salt in a quantity of a second carrier liquid, to produce aluminum oxide in a wetted copper salt impregnated state;

(d) at least partially drying the wetted copper salt impregnated aluminum oxide; and (e) calcining the dried copper salt impregnated aluminum oxide to at least partially convert the impregnated copper salt to copper oxide crystallites.

14. The method of claim 13, wherein the mechanically stable phase of aluminum oxide is selected from the group consisting of γ-alumina, δ-alumina, θ-alumina, α-alumina, and mixtures thereof.

15. The method of claim 13, wherein the mechanically stable phase of aluminum oxide is prepared by:

(a) mixing an initial phase of aluminum oxide with water;

(b) extruding hydrated aluminum oxide into a suitable form;

(c) at least partially drying the extruded hydrated aluminum oxide; and (d) calcining the dried extruded aluminum oxide at a temperature sufficient to convert the aluminum oxide to the mechanically stable phase of aluminum oxide.

16. The method of claim 15, which further comprises selecting wide pore alumina as the initial phase of aluminum oxide.

17. The method of claim 16, wherein the hydrated wide pore alumina is extruded into a trilobe form.

18. The method of claim 13, wherein the chelating agent is selected from the group consisting of ethylenediaminetetraacetic acid; tris(2-aminoethyl)amine; triethylenetetraamine; diethylenetriaminepentaacetic acid; 1,2-diaminocyclohexane-N,N,N',N'-tetraacetic acid; ethylene glycol bis(2-aminoethylether)-N,N,N',N'-tetraacetic acid; tetraethylenepentaamine; and salts thereof.

19. The method of claim 13, wherein ethylenediaminetetraacetic acid, diammonium salt is selected as the chelating agent.

20. The method of claim 19, wherein water is selected as the first carrier liquid.

21. The method of claim 20, wherein the first solution is adjusted to a concentration of the ethylenediaminetetraacetic acid, diammonium salt such that the amount of ethylenediaminetetraacetic acid, diammonium salt impregnated into the aluminum oxide is from about 0.1 g to about 0.3 g per gram of aluminum oxide.

22. The method of claim 13, wherein the wetted pre-doped aluminum oxide is dried by air drying at a temperature of from about 150° C. to about 205° C. for about 1 to about 4 hours.

23. The method of claim 13, wherein the at least one copper salt is selected from the group consisting of copper nitrate, copper formate, copper nitrite, copper nitride, copper cyanide, copper ferrocyanide, copper chloride, copper bromide, copper perchlorate, copper bromate, copper iodide, copper sulfide, copper sulfate, copper thiocyanate, copper carbonate, copper acetate, copper oxalate, copper butyrate, copper citrate, copper benzoate, copper borate, copper phosphate, copper carbide, copper chromate, copper tungstate, and any mixture thereof.

24. The method of claim 13, wherein copper nitrate is selected as the copper salt.

25. The method of claim 24, wherein water is selected as the second carrier liquid.

26. The method of claim 25, wherein the second solution is adjusted to a concentration of the copper nitrate from about 12 to about 25 weight percent.

27. The method of claim 13, wherein the wetted copper salt impregnated aluminum oxide is air dried at a temperature of from about 150° C. to about 205° C. for about 1 to about 4 hours.

28. The method of claim 13, wherein the dried, copper salt impregnated aluminum oxide is calcined at a temperature of from about 250° C. to about 540° C. for about 30 minutes to about 120 minutes.

29. The method of claim 13, further comprising the step of at least partially reducing the copper oxide crystallites with at least one reducing agent, wherein at least a portion of the copper oxide crystallites are thereby converted to elemental copper crystallites.

30. The method of claim 29, wherein hydrogen is selected as the reducing agent.

31. A method for preparing a catalyst, said method comprising the steps of:

(a) impregnating a mechanically stable phase of aluminum oxide with at least one copper salt by contacting the aluminum oxide with a solution, which solution comprises a quantity of the copper salt and a quantity of ammonia at least partially dissolved in water, to produce aluminum oxide in a wetted copper salt impregnated state;

(b) at least partially drying the wetted copper salt impregnated aluminum oxide; and (c) calcining the dried copper salt impregnated aluminum oxide to at least partially convert the impregnated copper salt to copper oxide crystallites.

32. The method of claim 31, wherein the mechanically stable phase of aluminum oxide is selected from the group consisting of γ-alumina, δ-alumina, θ-alumina, α-alumina, and any mixture thereof.

33. The method of claim 32, wherein the mechanically stable phase of aluminum oxide is prepared by:

(a) mixing an initial phase of aluminum oxide with water;

(b) extruding hydrated aluminum oxide into a suitable form;

(c) at least partially drying the extruded hydrated aluminum oxide; and (d) calcining the dried extruded aluminum oxide at a temperature sufficient to convert the aluminum oxide to the mechanically stable phase of aluminum oxide.

34. The method of claim 33, which further comprises selecting wide pore alumina as the initial phase of aluminum oxide.

35. The method of claim 34, wherein the hydrated wide pore alumina is extruded into a trilobe form.

36. The method of claim 31, wherein the copper salt is selected from the group consisting of copper nitrate, copper formate, copper nitrite, copper nitride, copper cyanide, copper ferrocyanide, copper chloride, copper bromide, copper perchlorate, copper bromate, copper iodide, copper sulfide, copper sulfate, copper thiocyanate, copper carbonate, copper acetate, copper oxalate, copper butyrate, copper citrate, copper benzoate, copper borate, copper phosphate, copper carbide, copper chromate, copper tungstate, and any mixture thereof.

37. The method of claim 31, wherein copper formate is chosen as the copper salt.

38. The method of claim 37, wherein the solution is adjusted to a concentration of the copper formate of from about 5 to about 20% by weight.

39. The method of claim 31, wherein the solution is adjusted to a concentration of the ammonia of from about 25% to about 34% by weight.

40. The method of claim 31, wherein the wetted copper salt impregnated aluminum oxide is air dried at a temperature of from about 150° C. to about 205° C. for about 1 to about 4 hours.

41. The method of claim 31, wherein the dried impregnated aluminum oxide is calcined at a temperature from about 250° C. to about 540° C. for about 30 minutes to about 120 minutes.

42. The method of claim 31, further comprising the step of: at least partially reducing the copper oxide crystallites with at least one reducing agent, wherein at least a portion of the copper oxide crystallites are converted to crystallites of elemental copper.

43. The method of claim 42, wherein hydrogen is selected as the reducing agent.

* * * * *